United States Patent
Bracken

(10) Patent No.: US 8,056,558 B2
(45) Date of Patent: Nov. 15, 2011

(54) PATIENT DELIVERY TUBE FOR HUMIDIFIED OXYGEN

(75) Inventor: Ronny Bracken, Monroe, GA (US)

(73) Assignee: C.R. Bard, Inc., Covington, GA (US)

( * ) Notice: Subject to any disclaimer, the term of this patent is extended or adjusted under 35 U.S.C. 154(b) by 1151 days.

(21) Appl. No.: 11/780,856

(22) Filed: Jul. 20, 2007

(65) Prior Publication Data

US 2010/0012121 A9    Jan. 21, 2010

Related U.S. Application Data

(60) Provisional application No. 60/807,832, filed on Jul. 20, 2006.

(51) Int. Cl.
*A61M 11/00* (2006.01)
(52) U.S. Cl. ............. 128/203.26; 261/101; 261/DIG. 65
(58) Field of Classification Search ............ 128/203.26, 128/201.13, 203.16, 203.17, 204.13, 204.17; 261/101, 104, DIG. 65
See application file for complete search history.

(56) References Cited

U.S. PATENT DOCUMENTS

| | | | |
|---|---|---|---|
| 6,367,472 B1 * | 4/2002 | Koch ..................... | 128/203.12 |
| 6,904,911 B2 * | 6/2005 | Gibertoni ............... | 128/201.13 |
| 6,976,489 B2 * | 12/2005 | Mantell et al. .......... | 128/204.17 |
| 7,428,902 B2 * | 9/2008 | Du et al. ................ | 128/204.17 |
| 7,476,212 B2 * | 1/2009 | Spearman et al. ........ | 604/23 |

* cited by examiner

*Primary Examiner* — Steven Douglas
(74) *Attorney, Agent, or Firm* — Knobbe Martens Olson & Bear LLP

(57) ABSTRACT

A patient delivery tube for the delivery of a heated, humidified gas. The patient delivery tube includes an elongated tubing member molded from a flexible polymer, said elongated tubing member comprising a first end, a second end and an axially aligned passageway extending therethrough and an electric heater comprising a conductive material, said electric heater arranged along said axially aligned passageway for perimetrically heating said axially aligned passageway. A method of delivering a heated, humidified gas to a patient is also provided.

18 Claims, 6 Drawing Sheets

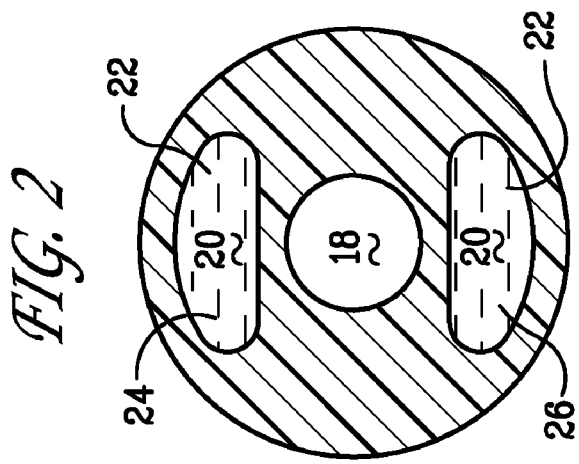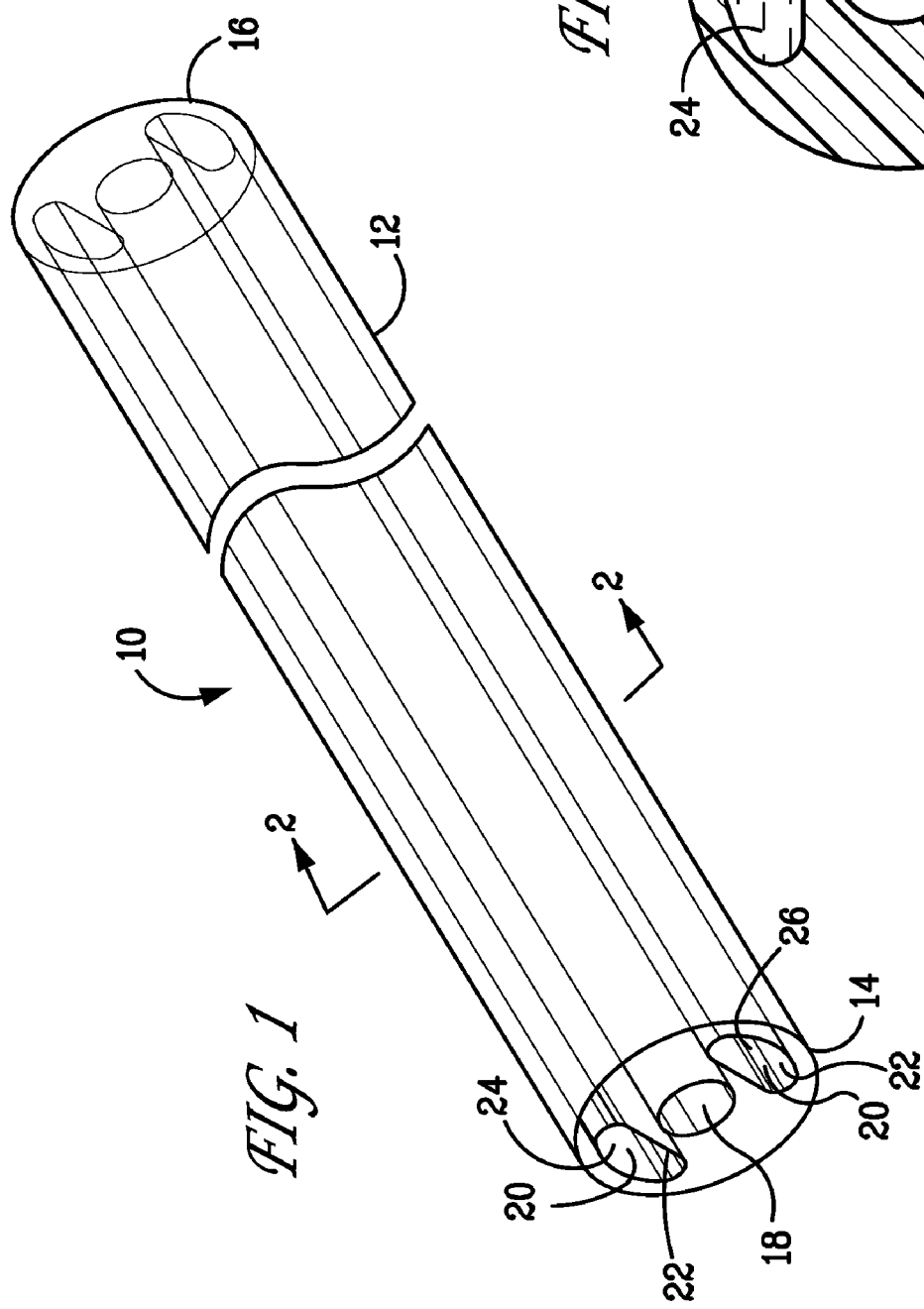

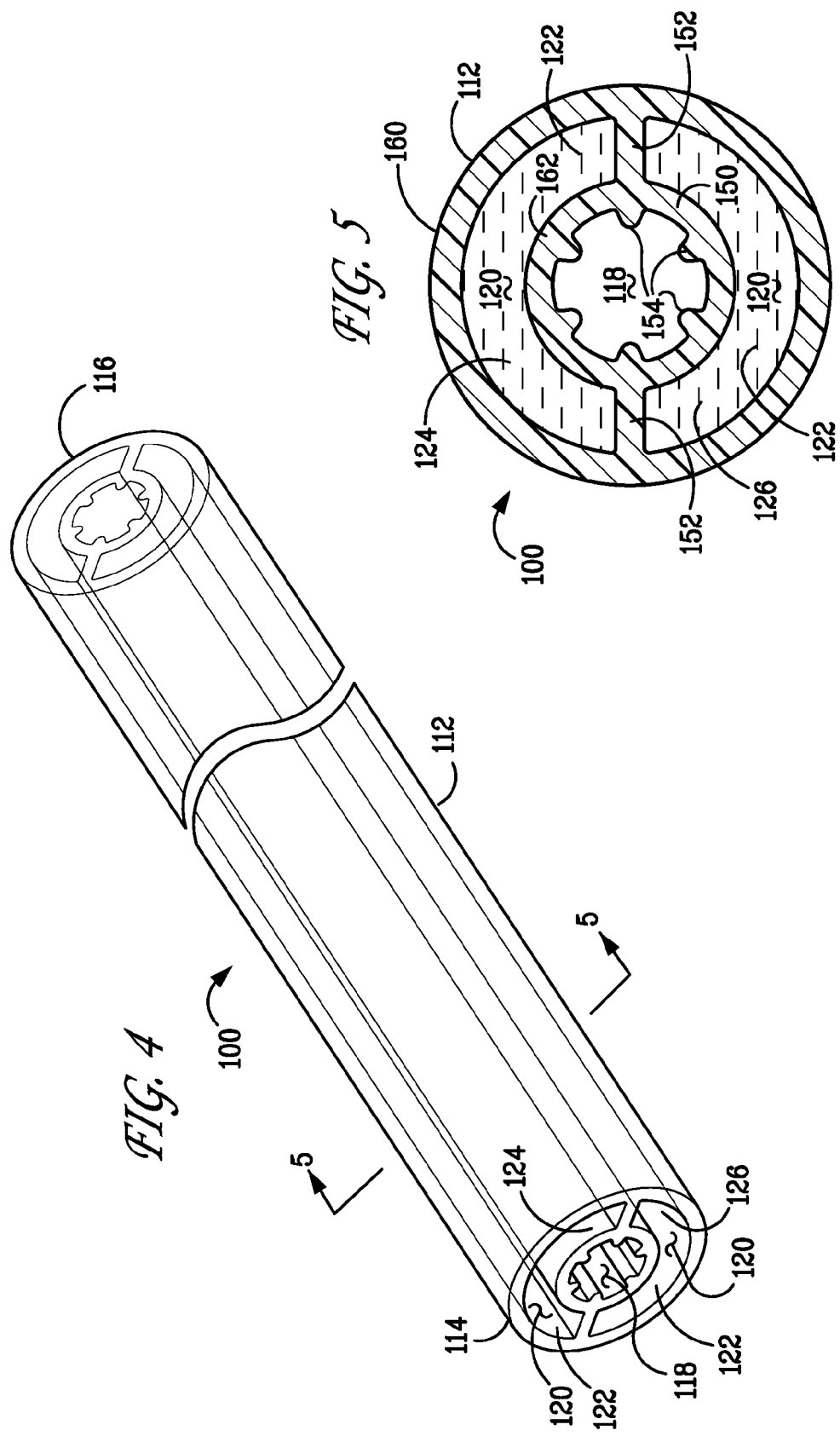

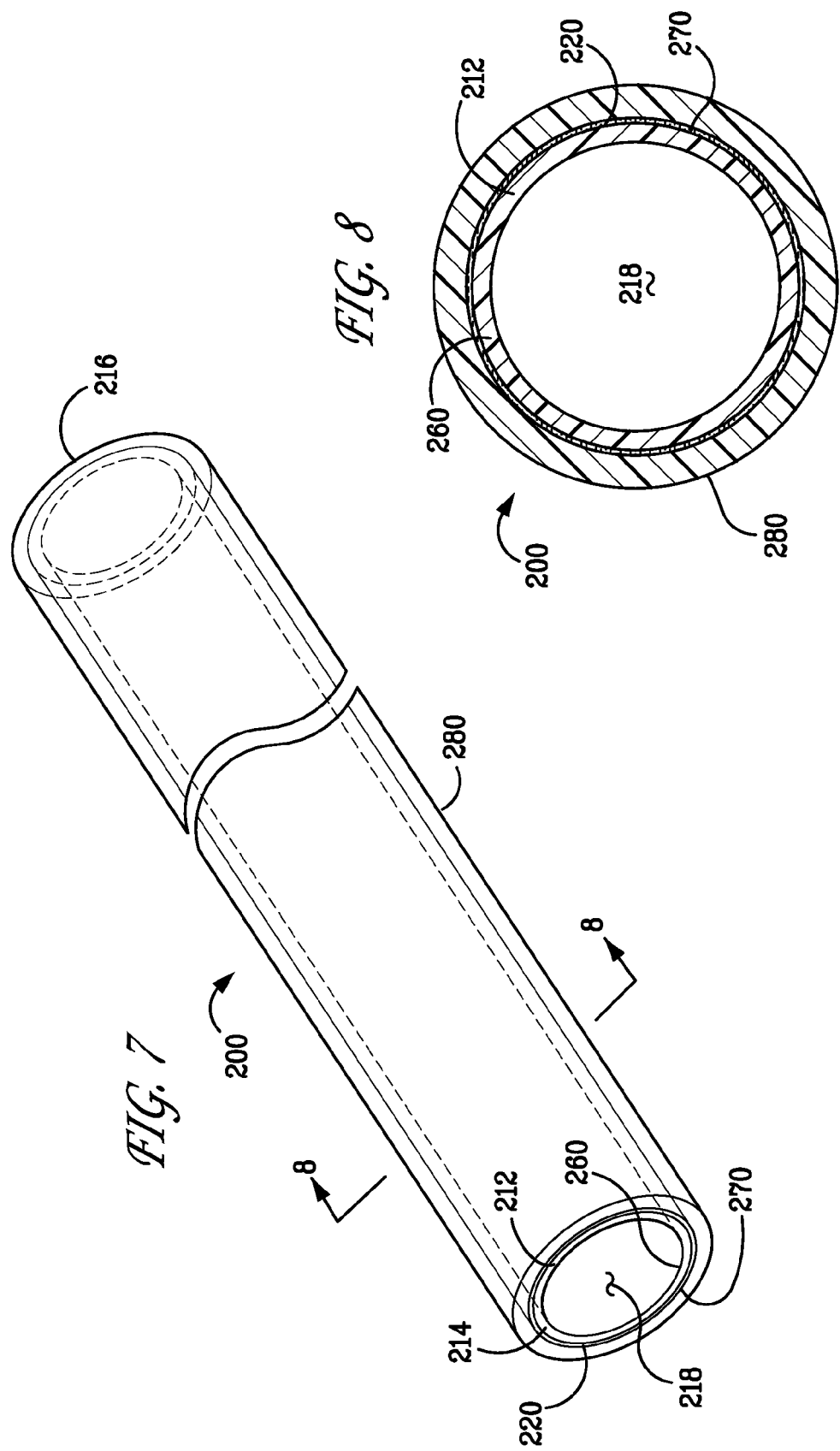

PATIENT DELIVERY TUBE FOR HUMIDIFIED OXYGEN

CROSS REFERENCE TO RELATED APPLICATIONS

This application claims the benefit of U.S. Provisional Application No. 60/807,832, filed Jul. 20, 2006.

The present invention relates to an apparatus and method for respiratory tract therapy. More particularly, this invention relates to an apparatus adapted to heat and humidify air and to deliver heated and humidified air to the respiratory tract of a human patient.

Oxygen therapy is a key treatment in respiratory care. Such therapy serves to increase oxygen saturation in tissues where the saturation levels are too low due to illness or injury. Some of the conditions in which oxygen therapy is used include hypoxemia, severe respiratory distress (e.g., acute asthma or pneumonia), severe trauma, acute myocardial infarction and short-term therapy, such as post-anesthesia recovery. Hyperbaric oxygen therapy is used in cases of gas gangrene, decompression sickness, air embolism, smoke inhalation, carbon monoxide poisoning and cerebral hypoxic events.

In the delivery of oxygen and oxygen-enriched air, it is recognized that significant discomfort is often experienced by the patient, especially when the air is delivered over an extended period of time. Moreover, it is generally known that it is far more beneficial for the patient to receive such gases under conditions of somewhat elevated heat and humidity, rather than to supply the patient with a cool dry gas. It has also been recognized that the delivery of air having relatively low absolute humidity can result in respiratory irritation It has been found, for example, that when the inhaled gas is both heated and humidified, the patient is more receptive to the gas, with other potential respiratory diseases minimized.

One example is rhinitis, which can be caused by viral infections such as the common cold, influenza and allergies. Rhinitis can also be caused by failure of the nasal defense system as the result of, for example, cystic fibrosis. The nasal defense system utilizes a layer of mucus that traps particles such as bacteria. Tiny cilia hairs on the cells of mucous membrane move the mucus with trapped particles to the back of the nose where it enters the throat and is swallowed. If this system fails because the mucus is insufficient or too thick, bacterial infection and inflammation can result.

The introduction of heated and humidified air into the respiratory tract helps to treat rhinitis by the thinning of mucus, which leads to improved secretion clearance. Also, high humidity promotes the healing of inflamed mucus-producing and ciliated cells. Also, high temperature is believed to reduce the rate of viral replication. Accordingly, breathing of heated and humidified air can be a beneficial treatment for many types of rhinitis.

Asthma remains a serious and growing public health problem. Asthma is not considered to be curable, and the treatment of asthma consists largely of attempts at control. The process underlying asthma appears to be inflammatory leading to hyper-reactivity of the airways when they constrict in response to a variety of stimuli. Although inhaled medications have been proposed to reduce inflammation and to relax the bronchial muscle directly, there have been concerns raised over abuse of the medications and the side-effects associated with such medications. Recently, it has been suggested that the delivery of warm humid air to the entire respiratory tract can be of benefit to asthma sufferers, without the risk and side-effects of the drugs in present use.

In the delivery of heated and humidified air to a patient, it may be desirable to reduce the precipitation of water and maintain a suitable air temperature In this regard, electrically heated hoses have been used to add additional heat to the flowing air, counteracting the heat lost along the length of the hose. Conventional electrically heated hoses or tubing employ a heating element, in the form of a solid or stranded resistance wire, which is either embedded in the wall or wound around the circumference of the hose. In some cases, the resistance wire is spirally wrapped around a supporting thread before it is wrapped around the hose. These hoses apply heat at the walls, which is communicated to the fluid passing within the hose by convection. Alternatively, the heating element may be loosely strung within the lumen of the hose. In this case, heat is conducted to the fluid passing within the lumen from the heating element through insulation placed over the heating element.

A problem particular to spirally wound heater wire elements is the formation of localized hot spots from variations in power density. The variation in power density is caused by inconsistency of the spiral pitch over a short section of the element. The winding pitch seems to be particularly difficult for manufacturers of this element to maintain and necessitates specialized testing and equipment to detect in a high speed extrusion operation. This localized hot spot can melt through the hose wall and pose a fire threat.

One design proposed to overcome these problems includes a flexible ribbon that spans the width of a flexible tubing and extends generally through the length of the tubing, the flexible ribbon carrying a heating element. The heating element proposed is an electrically conductive wire or plurality of wires, connected to a power supply in order to heat the flow of gas traveling within the tube. The flow is heated as it passes over and around the heating element. The flexible ribbon supporting the heating element can be integral with the tubing or comprise an insertable unit which fits into the tubing.

The U.S. Food and Drug Administration has issued a Safety Alert detailing the hazards of heated-wire breathing circuits. In this Alert, the FDA notes that it has learned of instances in which improperly used heated-wire breathing circuits have overheated, softened, or melted, causing diminished gas delivery, fires and burns to patients and caregivers.

In response to the aforementioned problems associated with heated-wire breathing circuits, a number of heated-water breathing circuits have been proposed. One such device includes a tubing assembly for delivering a gas to a patient from a supply unit having a gas outlet, a fluid outlet, and a fluid inlet, the tubing assembly including a tube having a gas passage to deliver gas toward a patient and a fluid passage to circulate heated fluid and transfer heat to gas in the gas passage. However, it must be noted that a direct interface between water and air must be avoided in such a system so that the output gas is substantially free of bacteria, viruses and allergens.

As such, there remains a need for an improved patient delivery tube and apparatus for respiratory tract therapy that overcomes the problems associated with current designs.

In one aspect, provided is a patient delivery tube for the delivery of at least one of a heated gas and a humidified gas. The patient delivery tube includes an elongated tubing member molded from a flexible polymer, the elongated tubing member comprising a first end, a second end and at least one axially aligned passageway extending therethrough and an electric heater comprising a conductive material, the electric heater arranged along the axially aligned passageway for perimetrically heating the axially aligned passageway.

According to one aspect, the gas is heated. According to another aspect, the gas is heated and humidified.

In another aspect, provided is a method of delivering at least one of a heated gas and a humidified gas to a patient. The method includes the steps of placing a patient delivery tube in communication with an airway of a patient, the patient delivery tube including an elongated tubing member molded from a flexible polymer, the elongated tubing member comprising a first end, a second end and at least one axially aligned passageway extending therethrough and an electric heater comprising a conductive material, the electric heater arranged along the axially aligned passageway for perimetrically heating the axially aligned passageway and delivering a heated, humidified gas to the patient delivery tube.

The patient delivery tubes disclosed herein may be provided with any number of lumens, including one, two, three, four or more lumens, and may be of any cross-section, including substantially circular, oval, octagonal, etc.

In one embodiment, the elongated tubing member includes first and second lumens positioned so as to at least partially surround the axially aligned passageway. The first and second lumens are filled with a conductive gel, so as to form an electric heater. The conductive gel may be formed by dispersing a plurality of conductive particles within a gelatinous dielectric medium, the conductive particles chosen from silver-coated nickel particles, silver-coated glass particles, carbon particles, silver spheres, silver flakes and mixtures thereof. The gelatinous dielectric medium may comprise a silicone gel In another embodiment, the elongated tubing member is a single lumen tube having an outer surface. The conductive material includes a conductive ink applied to the outer surface of the elongated tubing member A protective cover may be positioned over the outer surface of the elongated tubing member to insulate and protect the heater of the patient delivery tube. The conductive ink may be a positive temperature coefficient ink, capable of self regulation Alternatively, the conductive ink may be chosen from a carbon ink, a silver ink and blends thereof. When a carbon ink is employed, such an ink may have a resistivity of between about 25 to about 500 ohms per square cm at 15 microns dried film thickness. When a blend of carbon and silver inks is employed, such an ink may have a resistivity of between about 0.05 to about 25 ohms per square cm at 15 microns dried film thickness.

These and other features will be apparent from the description taken with reference to accompanying drawings.

BRIEF DESCRIPTION OF THE DRAWINGS

The invention is further explained in the description that follows with reference to the drawings illustrating, by way of non-limiting examples, various embodiments of the invention wherein:

FIG. 1 is a partial perspective view of one embodiment of a patient delivery tube, depicting a three lumen elongated tubing member;

FIG. 2 is a cross-sectional end view of the patient delivery tube of FIG. 1 taken along line 2-2 of FIG. 1;

FIG. 4 is a partial perspective view of another embodiment of a patient delivery tube, depicting another three lumen elongated tubing member;

FIG. 5 is a cross-sectional end view of the patient delivery tube of FIG. 4 taken along line 5-5 of FIG. 4;

FIG. 7 is a partial perspective view of another embodiment of a patient delivery tube, depicting a single lumen elongated tubing member;

FIG. 8 is a cross-sectional end view of the patient delivery tube of FIG. 7 taken along line 8-8 of FIG. 7.

Figure 3:
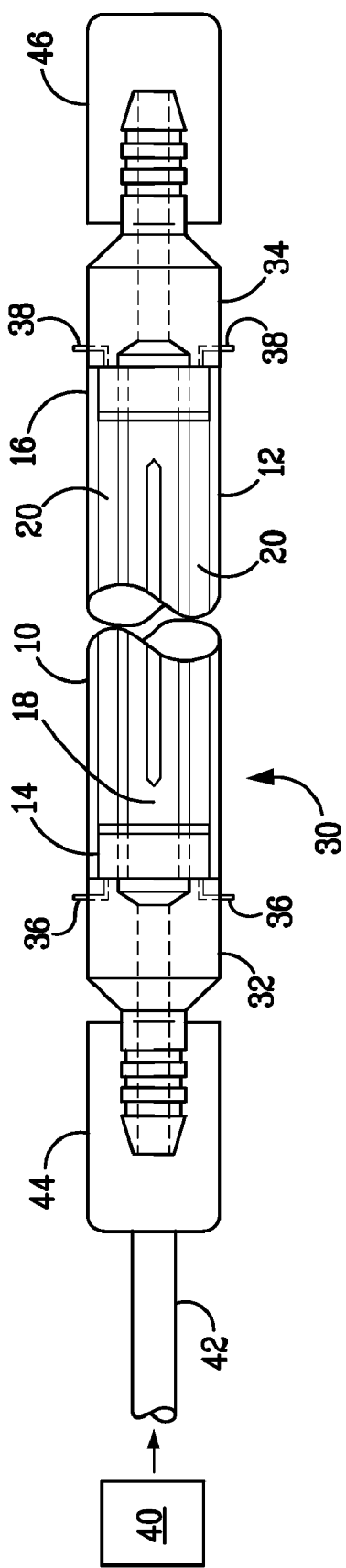
FIG. 3 is a side view of a patient delivery tube assembly employing the patient delivery tube of FIG. 1.

Various aspects will now be described with reference to specific embodiments selected for purposes of illustration. It will be appreciated that the spirit and scope of the patient delivery tube disclosed herein is not limited to the selected embodiments. Moreover, it is to be noted that the figures provided herein are not drawn to any particular proportion or scale, and that many variations can be made to the illustrated embodiments. Reference is now made to FIGS. 1-9, wherein like numerals are used to designate like parts throughout.

Referring now to FIGS. 1 and 2, an exemplary embodiment of a patient delivery tube 10 includes an elongated tubing member 12 molded from a flexible polymer. Elongated tubing member 12 includes a first end 14, a second end 16 and an axially aligned passageway 18, extending therethrough. Elongated tubing member 12 also includes an electric heater 20 comprising a conductive material 22. As shown, electric heater 20 is arranged along the axially aligned passageway 18 for perimetrically heating axially aligned passageway 18

Referring now to FIG. 3, a patient delivery tube assembly 30 that employs patient delivery tube 10 is shown. Patient delivery tube assembly 30 is utilized for delivering a heated, humidified gas from an apparatus 40 capable of providing heated, humidified air, oxygen or an air/oxygen blend. The air, oxygen or an air/oxygen blend is supplied by apparatus 40 to patient delivery tube assembly 30 via gas tube 42. Gas tube 42 includes a connector 44 for receiving patient delivery tube connector 32 of patient delivery tube assembly 30. As shown, a first patient delivery tube connector 32 mates with first end 14 of elongated tubing member 12 of patient delivery tube 10. A second patient delivery tube connector 34 mates with second end 16 of the elongated tubing member 12 for connection via connector 46, for example, to a conventional nasal cannula (not shown) for receipt by a patient. As will be described in more detail below, the patient delivery tube 10 is adapted to heat the gas as it is delivered to the respiratory tract of a patient.

As indicated above, the elongated tubing member includes an axially aligned passageway 18, or gas lumen, which is defined by the elongated tubing member 12 and runs from the first end 14, which serves as the gas inlet, to the second end 16, which serves as the gas outlet. The elongated tubing member 12 also includes an electric heater 20 that comprises a conductive material 22. As shown, conductive material 22 of electric 20 is contained within first lumen 24 and second lumen 26, with first lumen 24 and second lumen 26 positioned so as to at least partially surround the axially aligned passageway 18.

Conductive material 22 of electrical heater 20 includes a conductive gel-like material. As is known by those skilled in the art, a conductive gel is formed by dispersing a plurality of conductive particles within a gelatinous dielectric medium. In order to form a fully conductive gel, the concentration of the conductive particles in the dielectric medium should be at least equal to or above the percolation threshold; the percolation threshold being the lower limit of a volumetric concentration of randomly distributed conductive particles within a dielectric medium which would result in bulk conductivity. The conductivity threshold is generally on the order of 20 to 25% by volume of the conductive particles in a dielectric medium. The concentration of conductive particles may be between about 25 and about 30%, by volume of conductive gel. Nevertheless, it should be noted that anisotropic, or unidirectional conductivity may be achieved in thin films by limiting the concentration of the conductive particles to the order of about 10% by volume.

Overall properties of the conductive gel are attributable to the dielectric medium employed. This dielectric medium may be selected so that the conductive gel will exhibit a certain memory-like viscosity. The dielectric gel may also tend to self-heal and return to its original shape. The conductive gel may be conformable to the interface between the connectors 32 and 34 and the electrical conductors 36 and 38. In other words, the gelatinous dielectric medium may form a coherent nonflowable mass.

While a wide variety of gels are available that would have utility in the patient delivery tube 10 disclosed herein, silicone gels exhibit the physical characteristics described hereinabove. One such silicone gel is a dielectric two-component transparent silicone encapsulant specifically marketed under the trademark Sylgard® 527 by Dow Corning Corporation of Midland, Mich. When the two components of this material are mixed in a one-to-one ratio, the consequent material forms a cushioning, self-healing, resilient gel-like mass. This gel has some of the stress relief and self-healing properties of a liquid but is dimensionally stable and nonflowing, enabling the conductive particles to remain uniformly distributed within the gel. The material is hydrophobic and forms a seal with the electrical conductors 36 and 38, inserted therein. The material is deformable and will conform to the contours of the first lumen 24 and second lumen 36 into which it is deposited, as well as conforming to the interface with conductors 36 and 38, inserted into engagement therewith.

The conductive particles distributed within the gel to form the conductive gel of conductive material 22 can comprise any of a number of conventionally available conductive particles. For purposes of example and not by way of limitation, silver-coated nickel particles, silver-coated glass particles, solid silver spheres, silver flakes, carbon particles or mixtures thereof, can be employed.

Referring still to FIG. 3, in use current is applied to conductors 36 and 38 of a first patient delivery tube connector 32 and second patient delivery tube connector 34, respectively, of patient delivery tube assembly 30. As described above, conductors 36 and 38 are in electrical communication with the conductive material 22 contained within first lumen 24 and second lumen 26 of heater 20 and produces heat as current is applied thereto. The heat so produced is thereby transferred from the heater 20 to the gas in the axially aligned passageway 18, so as to deliver heated and humidified air to the respiratory tract of a patient.

The patient delivery tube 10 described herein may be employed with an apparatus that provides a source for heated, and/or humidified air, oxygen or blends thereof, such as apparatus 40. Such an apparatus may be adapted for use in a variety of settings and for transport between locations. The apparatus 40 may be used in the home by a patient and at the patient's bedside, if desired. The apparatus 40 can also be used in hospitals, clinics, and other settings, as well. An apparatus 40 capable of supplying humidified air is known in the art The patient delivery tube assembly 30 may be designed so that it can be used by a particular patient and then discarded after one or any number of uses. The patient delivery tube assembly 30 provides a passageway for the flow of humidified air to the patient's respiratory tract. The patient delivery tube assembly 30 may be connected to a nasal cannula (not shown) that extends from patient delivery tube assembly 30 to the patient's respiratory tract during use. Nasal cannula and associated fittings used for supplying air to the nares of a patient are readily available components that are well known in the art.

Patient delivery tube 10 can be formed from a variety of materials and by a variety of processes Patient delivery tube 10 may be formed from a polymeric material such as polyurethane, polyethylene, polypropylene, polyester and copolymers, terpolymers and blends thereof. Patient delivery tube 10 may be formed from a polyetherurethane, such as Pellethane® 2363-80AE, which has a durometer of Shore 80A. Pellethane® is available from The Dow Chemical Company of Midland, Mich. According to various embodiments patient delivery tube 10 is clear to permit a degree of visualization and enable a user to ascertain that sufficient heat is being applied so that no condensation occurs. Patient delivery tube 10 is suitably extruded in long lengths having a substantially constant cross-sectional shape. Although various lengths are contemplated for patient delivery tube 10, a length of about 10 feet will provide adequate performance and adequate versatility to the patient. Other lengths are of course contemplated, depending on specific circumstances, the length of nasal cannula, heat transfer characteristics and matters of cost and design choice.

In operation, gas (air, oxygen, or some combination) is supplied to the apparatus 40 via a tube (not shown) at about 50 psi maximum pressure. The gas flow can be regulated by a user-supplied restricting valve at the source of the gas so that it can be controlled between flows of about 5 to about 50 l/min, or between about 5 to about 40 l/min A patient delivery tube assembly 30 can be attached at the front of the apparatus 40 via a manifold (not shown) that interfaces to a gas supply port. The apparatus 40 can be designed to operate on standard 115VAC, 60 Hz. A standard hospital grade power cord can be supplied with the unit. The apparatus 40 can also employ a microprocessor to control heating, gas flow, gas pressure, humidification, etc., as those skilled in the art can readily understand.

The apparatus 40 is adapted to operate within predetermined parameters. In one exemplary embodiment, the apparatus can operate in a controlled air output temperature range of from about 35° C. to about 43° C.; an operating flow range of about 5 to about 40 l/min; a gas pressure not to exceed about 60 psi; and a gas composition of dry air and/or oxygen, from about 21% $O_2$ to about 100% $O_2$. According to various embodiments, gas humidification exceeds about 95% relative humidity.

Referring now to FIGS. 4 and 5, another exemplary embodiment of a patient delivery tube 100 includes an elongated tubing member 112 molded from a flexible polymer. Elongated tubing member 112 includes a first end 114, a second end 116 and an axially aligned passageway 118, extending therethrough. Elongated tubing member 112 also includes an electric heater 120 comprising a conductive material 122. As shown, electric heater 120 is arranged along the axially aligned passageway 118 for perimetrically heating axially aligned passageway 118.

Referring specifically now to FIG. 5, which provides a cross-sectional end view of elongated tubing member 112, further details of patient delivery tube 100 will now be described. Patient delivery tube 100 includes a substantially circular outer wall 160 spaced concentrically around a substantially circular inner wall 162. Boundary walls 152 extend from the inner surface of outer wall 160 to the outer surface of inner wall 162. A plurality of longitudinally extending ribs 154 extends radially inwardly from the inner surface of inner wall 162 and along the axis of elongated tubing member 112.

Inner wall 162 and ribs 154 together serve to define axially aligned passageway 118 that extends along the length of elongated tubing member 112. In the embodiment illustrated in FIG. 5, six ribs 154 are uniformly spaced. Ribs 154 additionally serve to prevent constriction of axially aligned passageway 118 in the event that elongated tubing member 112 is bent in use or otherwise kinked unintentionally. Outer wall 160 and inner wall 162 together define with boundary walls 152 a first lumen 124 and a second lumen 126 that have a substantially arcuate cross-sectional shape and that substantially surround axially aligned passageway 118.

Figure 6:
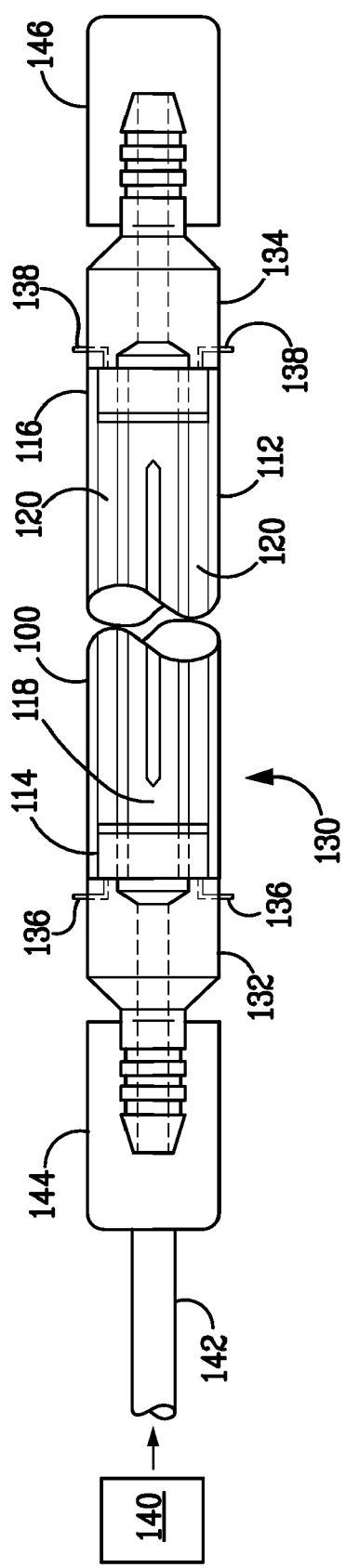
FIG. 6 is a side view of a patient delivery tube assembly employing the patient delivery tube of FIG. 4.

Referring now to FIG. 6, a patient delivery tube assembly 130 that employs patient delivery tube 100 is shown. Patient delivery tube assembly 130 is utilized for delivering a heated, humidified gas from an apparatus 140 capable of providing heated and/or humidified air, oxygen or an air/oxygen blend. The air, oxygen or an air/oxygen blend is supplied by apparatus 140 to patient delivery tube assembly 130 via gas tube 142. Gas tube 142 includes a connector 144 for receiving patient delivery tube connector 132 of patient delivery tube assembly 130. According to another embodiment (not shown), connector 132 is inserted directly into apparatus 140. As shown, a first patient delivery tube connector 132 mates with first end 114 of elongated tubing member 112 of patient delivery tube 100. A second patient delivery tube connector 134 mates with second end 116 of the elongated tubing member 112 for connection via connector 146, for example, to a conventional nasal cannula (not shown) for receipt by a patient. As will be described in more detail below, the patient delivery tube 100 is adapted to heat the gas as it is delivered to the respiratory tract of a patient.

The elongated tubing member includes an axially aligned passageway 118, or gas lumen, which is defined by the elongated tubing member 112 and runs from the first end 114, which serves as the gas inlet, to the second end 16, which serves as the gas outlet. The elongated tubing member 112 also includes an electric heater 120 that comprises a conductive material 122 As shown, conductive material 122 of electric 120 is contained within first lumen 124 and second lumen 126, with first lumen 124 and second lumen 126 positioned so as to at least partially surround the axially aligned passageway 118.

As with the embodiment depicted in FIGS. 1-3, conductive material 122 of electrical heater 120 includes a conductive gel-like material formed by dispersing a plurality of conductive particles within a gelatinous dielectric medium. In order to form a fully conductive gel, the concentration of the conductive particles in the dielectric medium should be at least equal to or above the percolation threshold; the percolation threshold being the lower limit of a volumetric concentration of randomly distributed conductive particles within a dielectric medium which would result in bulk conductivity. The conductivity threshold is generally on the order of 20 to 25% by volume of the conductive particles in a dielectric medium. The concentration of conductive particles may be between about 25 and about 30%, by volume of conductive gel.

Overall properties of the conductive gel are attributable to the dielectric medium employed. This dielectric medium may be selected so that the conductive gel will exhibit a certain memory-like viscosity. The dielectric gel may also tend to self-heal and return to its original shape. The conductive gel may be conformable to the interface between the connectors 132 and 134 and the electrical conductors 136 and 138. In other words, the gelatinous dielectric medium may form a coherent nonflowable mass.

While a wide variety of gels are available that would have utility in the patient delivery tube 100 disclosed herein, silicone gels exhibit the physical characteristics described hereinabove. One such silicone gel, is a dielectric two-component transparent silicone encapsulant specifically marketed under the trademark Sylgard® 527 by Dow Corning Corporation of Midland, Mich. When the two components of this material are mixed in a one-to-one ratio, the consequent material forms a cushioning, self-healing, resilient gel-like mass. This gel has some of the stress relief and self-healing properties of a liquid but is dimensionally stable and nonflowing, enabling the conductive particles to remain uniformly distributed within the gel. The material is hydrophobic and forms a seal with the electrical conductors 136 and 138, inserted therein. The material is deformable and will conform to the contours of the first lumen 124 and second lumen 136 into which it is deposited, as well as conforming to the interface with conductors 136 and 138, inserted into engagement therewith.

The conductive particles distributed within the gel to form the conductive gel of conductive material 122 can comprise any of a number of conventionally available conductive particles. For purposes of example and not by way of limitation, silver-coated nickel particles, silver-coated glass particles, solid silver spheres, silver flakes, carbon particles or mixtures thereof, can be employed.

Still referring to FIG. 6, in use, current is applied to conductors 136 and 138 of a first patient delivery tube connector 132 and second patient delivery tube connector 134, respectively, of patient delivery tube assembly 130. As described above, conductors 136 and 138 are in electrical communication with the conductive material 122 contained within first lumen 124 and second lumen 126 of heater 120 and produces heat as current is applied thereto. The heat so produced is thereby transferred from the heater 120 to the gas in the axially aligned passageway 118, so as to deliver heated and humidified air to the respiratory tract of a patient. This arrangement can provide highly efficient heat transfer from the heater 120 to the flowing gas or air.

The patient delivery tube 100 described herein may be employed with an apparatus that provides a source for heated, humidified air, oxygen or blends thereof such as apparatus 140. Such an apparatus may be adapted for use in a variety of settings and for transport between locations. The apparatus 140 may be used in the home by a patient and at the patient's bedside, if desired. The apparatus 140 can also be used in hospitals, clinics, and other settings, as well.

The patient delivery tube assembly 130 may be designed so that it can be used by a particular patient and then discarded after one or any number of uses. The patient delivery tube assembly 130 provides a passageway for the flow of humidified air to the patient's respiratory tract. The patient delivery tube assembly 130 may be connected to a nasal cannula (not shown) that extends from patient delivery tube assembly 130 to the patient's respiratory tract during use. Nasal cannula and associated fittings used for supplying air to the nares of a patient are readily available components that are well known in the art.

Patient delivery tube 100 can be formed from a variety of materials and by a variety of processes. Patient delivery tube 100 may be formed from a polymeric material such as polyurethane, polyethylene, polypropylene, polyester and blends thereof. Patient delivery tube 100 may be formed from a polyetherurethane, such as Pellethane® 2363-80AE, which has a durometer of Shore 80A. Pellethane® is available from The Dow Chemical Company of Midland, Mich. Patient delivery tube 100 is preferably clear to permit some visualization and enable a user to ascertain that sufficient heat is being applied so that no condensation occurs. Patient delivery tube 100 is preferably extruded in long lengths having a substantially constant cross-sectional shape. Although various lengths are contemplated for patient delivery tube 100, a length of about 10 feet will provide adequate performance and adequate versatility to the patient. Other lengths are of course contemplated, depending on specific circumstances, the length of nasal cannula, heat transfer characteristics and matters of cost and design In operation, gas (air, oxygen, or some combination) is supplied to the apparatus 140 via a tube (not shown) at about 50 psi maximum pressure. The gas flow can be regulated by a user-supplied restricting valve at the source of the gas so that it can be controlled between flows of about 5 to 50 l/min, or between about 5 to 40 l/min. A patient delivery tube assembly 130 can be attached at the front of the apparatus 140 via a manifold (not shown) that interfaces to a gas supply port. The apparatus 140 can be designed to operate on standard 115VAC, 60 Hz. A standard hospital grade power cord can be supplied with the unit. The apparatus 140 can also employ a microprocessor to control heating, humidification, gas flow, gas pressure, etc., as those skilled in the art can readily understand.

The apparatus 140 is adapted to operate within predetermined parameters. In one exemplary embodiment, the apparatus can operate in a controlled air output temperature range of from about 35° C. to about 43° C.; an operating flow range of about 5 to about 40 l/min.; a gas pressure not to exceed about 60 psi; and a gas composition of dry air and/or oxygen, from about 21% $O_2$ to about 100% $O_2$. According to various embodiments, as humidification exceeds about 95% relative humidity.

Referring now to FIGS. 7 and 8, an exemplary embodiment of a patient delivery tube 200 includes an elongated tubing member 212 molded from a flexible polymer. Elongated tubing member 212 includes a first end 214, a second end 216 and an axially aligned passageway 218, extending therethrough. Elongated tubing member 212 also includes an electric heater 220 comprising a conductive material 270. As shown, electric heater 220 is arranged along the axially aligned passageway 218 for perimetrically heating axially aligned passageway 218.

Figure 9:
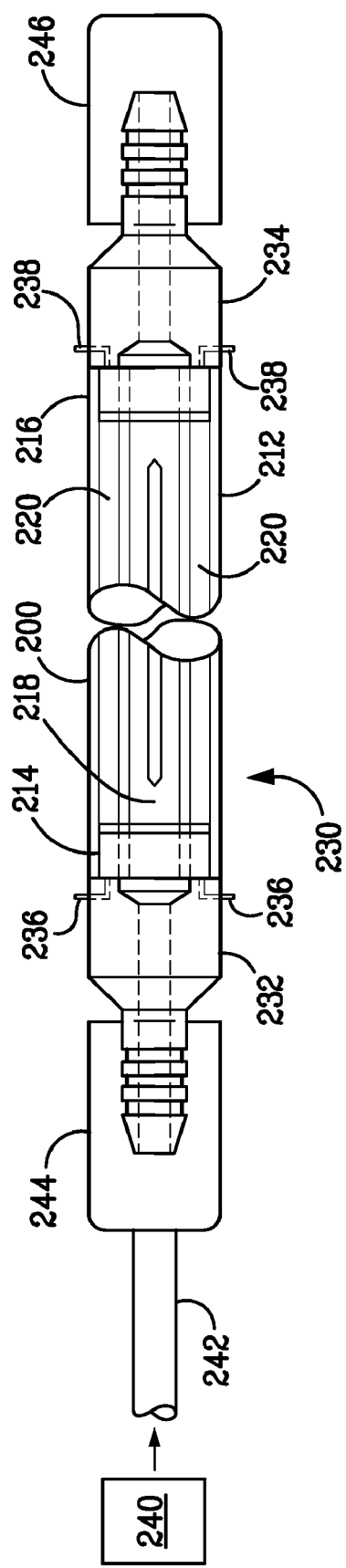
FIG. 9 is a side view of a patient delivery tube assembly employing the patient delivery tube of FIG. 7.

Referring now to FIG. 9, a patient delivery tube assembly 230 that employs patient delivery tube 200 is shown. Patient delivery tube assembly 230 is utilized for delivering a heated, humidified gas from an apparatus 240 capable of providing heated and/or humidified air, oxygen or an air/oxygen blend. The air, oxygen or an air/oxygen blend is supplied by apparatus 240 to patient delivery tube assembly 230 via gas tube 242. Gas tube 242 includes a connector 244 for receiving patient delivery tube connector 232 of patient delivery tube assembly 230. As shown, a first patient delivery tube connector 232 mates with first end 214 of elongated tubing member 212 of patient delivery tube 200. A second patient delivery tube connector 234 mates with second end 216 of the elongated tubing member 212 for connection via connector 246, for example, to a conventional nasal cannula (not shown) for receipt by a patient. As will be described in more detail below, the patient delivery tube 200 is adapted to heat the gas as it is delivered to the respiratory tract of a patient.

As indicated above, the elongated tubing member includes an axially aligned passageway 218, or gas lumen, which is defined by the elongated tubing member 212 and runs from the first end 214, which serves as the gas inlet, to the second end 16, which serves as the gas outlet. The elongated tubing member 212 also includes an electric heater 220 that comprises a conductive material 270.

In the embodiment depicted in FIGS. 7-9, the conductive material 270 comprises a conductive ink, which will be explained in more detail below. As shown, conductive material 270 of electric heater 220 is applied to outer surface 260 of elongated tubing member 212, so as to at least partially or fully surround the axially aligned passageway 218. A wide variety of conductive inks have utility in the fabrication of electric heater 220. Carbon-based inks, silver-based inks and mixtures thereof may be employed. Positive temperature coefficient (PTC) inks may also be employed in cases where it is desirable that heater 220 regulates itself. PTC inks can accomplish this since the resistance of the ink increases as the temperature rises, thus reducing the power density. PTC inks are usually based on highly crystalline resins such as fluoropolymers. Such inks are available from Coates, a division of Sun Chemical Corporation, of Parsippany, N.J., Dow Corning Corporation of Midland, Mich. and other sources.

With regard to the design of heater 220, it should be noted that the more electrically resistive the ink, the more difficult it is to manufacture. Greater fluctuations in current density are also likely with very resistive inks. As such, the blending of different inks can serve to obtain the desired resistance. Very resistive inks are also more likely to fail due to tracking; a condition where a favored electrical path results in a very high local current density and breakdown. Typical resistivities for carbon inks are from about 25 to about 500 ohms per square unit at 15 microns dried film thickness (DFT). More conductive inks can be made with a blend of carbon and silver inks ranging from about 0.05 to about 25 ohms per square unit.

A highly conductive silver ink, such as is available from Dow Corning of Midland, Mich., may also be employed. Such inks are available in both thermoset and thermoplastic forms that incorporate bis-A polymers and are highly filled with silver to enhance conductivity. These inks may be applied by screen-printing and other techniques. Within the thermosetting inks, additives are used that act upon the silver particles to increase the particle-to-particle contact. The thermoplastic inks use additives to achieve a tighter structure and more intimate particle-to-particle contact. Each result in high electrical conductivity levels.

A flexible tubular cover 280 can be installed over the conductive ink coated outer surface 260 of elongated tubing member 212 to insulate and protect electric heater 220. PTC inks should be covered with a material that has a similar coefficient of thermal expansion as the ink itself.

Still referring to FIG. 9, the electrodes 236 and 238 may be formed from a material such as copper or silver. Copper has the advantage in both conductivity and solderability, although silver can be applied as an ink, and may therefore be more cost effective. In use, current is applied to conductors 236 and 238 of a first patient delivery tube connector 232 and second patient delivery tube connector 234, respectively, of patient delivery tube assembly 230. As described above, conductors 236 and 238 are in electrical communication with the conductive material 270 of heater 220 and produces heat as current is applied thereto. The heat so produced is thereby transferred from the heater 220 to the gas in the axially aligned passageway 218, so as to deliver heated and humidified air to the respiratory tract of a patient.

The patient delivery tube 200 described herein may be employed with an apparatus that provides a source for heated, humidified air, oxygen or blends thereof, such as apparatus 240. Such an apparatus may be adapted for use in a variety of settings and for transport between locations. The apparatus 240 may be used in the home by a patient and at the patient's bedside, if desired. The apparatus 240 can also be used in hospitals, clinics, and other settings, as well.

The patient delivery tube assembly 230 may be designed so that it can be used by a particular patient and then discarded after one or any number of uses. The patient delivery tube assembly 230 provides a passageway for the flow of humidified air to the patient's respiratory tract. The patient delivery tube assembly 230 may be connected to a nasal cannula (not shown) that extends from patient delivery tube assembly 230 to the patient's respiratory tract during use. Nasal cannula and associated fittings used for supplying air to the nares of a patient are readily available components that are well known in the art.

Patient delivery tube 200 can be formed from a variety of materials and by a variety of processes. Patient delivery tube 200 may be formed from a polymeric material such as polyurethane, polyethylene, polypropylene, polyester and copolymers, terpolymers and blends thereof. Patient delivery tube 10 may be formed from a polyetherurethane, such as Pellethane® 2363-80AE, which has a durometer of Shore 80A. Pellethane® is available from The Dow Chemical Company of Midland, Mich. Patient delivery tube 200 is preferably extruded in long lengths having a substantially constant cross-sectional shape. Although various lengths are contemplated for patient delivery tube 200, a length of about 10 feet will provide adequate performance and adequate versatility to the patient. Other lengths are of course contemplated, depending on specific circumstances, the length of nasal cannula, heat transfer characteristics and matters of cost and design choice.

In operation, gas (air, oxygen, or some combination) is supplied to the apparatus 240 via a tube (not shown) at about 50 psi maximum pressure. The gas flow can be regulated by a user-supplied restricting valve at the source of the gas so that it can be controlled between flows of about 5 to 50 l/min, or between about 5 to 40 l/min. A patient delivery tube assembly 230 can be attached at the front of the apparatus 240 via a manifold (not shown) that interfaces to a gas supply port. The apparatus 240 can be designed to operate on standard 115VAC, 60 Hz. A standard hospital grade power cord can be supplied with the unit. The apparatus 240 can also employ a microprocessor to control heating, humidification, gas flow, gas pressure, etc., as those skilled in the art can readily understand.

The apparatus 240 is adapted to operate within predetermined parameters. In one exemplary embodiment, the apparatus can operate in a controlled air output temperature range of from about 35° C. to about 43° C.; an operating flow range of about 5 to about 40 l/min.; a gas pressure not to exceed about 60 psi; and a gas composition of dry air and/or oxygen, from about 21% $O_2$ to about 100% $O_2$. Gas humidification should preferably exceed about 95% relative humidity.

The patient delivery tubes disclosed herein can yield significant benefits when used for the treatment of the respiratory tract or for respiratory tract therapy. The patient delivery tubes disclosed herein can be uniquely adapted for the introduction of heated and humidified air to the respiratory tract of a human patient. Home use, hospital and clinical use are contemplated.

The introduction of heated and humidified air by using the patient delivery tubes disclosed herein can provide several unique advantages as compared to conventional humidifiers in connection with the treatment of rhinitis and other respiratory tract conditions. The use of a temperature-controlled patient delivery tube of the type disclosed herein can ensure that saturated air is delivered to the nose at body temperature or higher without heat loss or condensation, and a high flow rate of heated and humidified air ensures that almost all of the air breathed by a patient is heated and humidified with little or no entrained room air. These benefits can be accomplished by delivering air through a nasal cannula so that the patient can continue normal activities with minimal interference.

The patient delivery tubes disclosed herein can provide relief to people who suffer from asthma. Conventionally, asthma sufferers are recommended to keep humidity low because dust mites are more common in moist environments Accordingly, the system according to this invention provides the benefits of warm humid air in the entire respiratory tract without the problems associated with high ambient humidity A supply of room air saturated with water vapor at about 40° C. directly to the airway via a nasal cannula, thereby avoiding problems of condensation and cooling associated with conventional delivery of humidified air, reduces nasal irritation by eliminating drying and cooling of the nasal mucosa and pharynx, and is therefore therapeutic for asthma and rhinitis. More specifically, a patient may be fitted with a nasal cannula, and air is delivered to the patient at a flow rate of up to about 20 liters or more per minute at about 40° C., wherein the air is about 100% humidified.).

All patents, test procedures, and other documents cited herein, including priority documents, are fully incorporated by reference to the extent such disclosure is not inconsistent with this invention and for all jurisdictions in which such incorporation is permitted.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the invention, including all features which would be treated as equivalents thereof by those skilled in the art to which the invention pertains.

What is claimed is:

1. A patient delivery tube for the delivery of a heated, humidified gas, comprising:
   (a) an elongated tubing member molded from a flexible polymer, said elongated tubing member comprising a first end, a second end and at least one axially aligned passageway extending therethrough; and
   (b) an electric heater comprising a conductive material, said electric heater arranged along said axially aligned passageway for perimetrically heating said axially aligned passageway, wherein said conductive material of said electric heater comprises a conductive gel, said conductive gel being contained within said elongated tubing member.

2. The patient delivery tube of claim 1, wherein said flexible polymer is chosen from polyurethane, polyethylene, polypropylene, polyester, and copolymers, terpolymers and blends thereof.

3. The patient delivery tube of claim 2, wherein said elongated tubing member further comprises first and second lumens, said first and second lumens positioned so as to at least partially surround said axially aligned passageway.

4. The patient delivery tube of claim 1, wherein said conductive gel is formed by dispersing a plurality of conductive particles within a gelatinous dielectric medium.

5. The patient delivery tube of claim 4, wherein said conductive particles are chosen from silver-coated nickel particles, silver-coated glass particles, carbon particles, silver spheres, silver flakes and mixtures thereof.

6. The patient delivery tube of claim 5, wherein said gelatinous dielectric medium comprises silicone gel.

7. The patient delivery tube of claim 2, wherein said elongated tubing member is a single lumen tube having an outer surface.

8. The patient delivery tube of claim 7, further comprising an elongated protective cover, wherein said elongated protective cover is positioned over said outer surface of said elongated tubing member.

9. A method of delivering a heated, humidified gas to a patient comprising:
   (a) placing a patient delivery tube in communication with an airway of a patient; the patient delivery tube comprising an elongated tubing member molded from a flexible polymer, the elongated tubing member comprising a first end, a second end and at least one axially aligned passageway extending therethrough; and an electric heater comprising a conductive material, the electric heater arranged along the axially aligned passageway for perimetrically heating the axially aligned passageway, wherein the conductive material of the electric heater comprises a conductive gel, the conductive gel being contained within the elongated tubing member;
   (b) delivering a heated, humidified gas to the patient delivery tube.

10. The method of claim 9, wherein the flexible polymer is chosen from polyethylene, polypropylene, polyester, and copolymers and terpolymers thereof.

11. The method of claim 10, wherein the elongated tubing member further comprises first and second lumens, the first and second lumens positioned so as to at least partially surround the axially aligned passageway.

12. The method of claim 9, wherein the conductive gel is formed by dispersing a plurality of conductive particles within a gelatinous dielectric medium.

13. The method of claim 12, wherein the conductive particles are chosen from silver-coated nickel particles, silver-coated glass particles, carbon particles, silver spheres, silver flakes and mixtures thereof.

14. The method of claim 13, wherein the gelatinous dielectric medium comprises silicone gel.

15. The method of claim 10, wherein the elongated tubing member is a single lumen tube having an outer surface.

16. The method of claim 15, further comprising an elongated protective cover, wherein the elongated protective cover is positioned over the outer surface of the elongated tubing member.

17. A patient delivery tube for the delivery of a heated, humidified gas, comprising:
   an elongated tubing member molded from a flexible polymer, said elongated tubing member comprising a first end, a second end and at least one axially aligned passageway extending therethrough; and
   a conductive gel disposed within the elongated tubing member and along said at least one axially aligned passageway for perimetrically heating said axially aligned passageway.

18. The patient delivery tube of claim 17 further comprising an electric heater, said conductive gel being disposed within said electric heater.

* * * * *